United States Patent [19]

Scholl et al.

[11] 4,230,876

[45] Oct. 28, 1980

[54] PROCESS FOR THE PREPARATION OF URETHANES

[75] Inventors: Hans-Joachim Scholl, Cologne; Armin Zenner, Dormagen, both of Fed. Rep. of Germany

[73] Assignee: Bayer Aktiengesellschaft, Leverkusen, Fed. Rep. of Germany

[21] Appl. No.: 13,638

[22] Filed: Feb. 21, 1979

[30] Foreign Application Priority Data

Mar. 2, 1978 [DE] Fed. Rep. of Germany ....... 2808990

[51] Int. Cl.$^3$ ............................................ C07C 125/07
[52] U.S. Cl. ...................................... 560/25; 560/24; 560/27; 560/28
[58] Field of Search ........................ 560/25, 24, 27, 28

[56] References Cited

U.S. PATENT DOCUMENTS

| 3,895,054 | 7/1975 | Zajacek et al. | 560/25 |
| 3,956,360 | 5/1976 | Zajacek et al. | 560/25 |
| 3,993,685 | 11/1976 | Zajacek et al. | 560/25 |
| 4,080,365 | 3/1978 | Hirai et al. | 560/25 |
| 4,130,633 | 12/1978 | Shawl et al. | 560/25 |
| 4,170,708 | 10/1979 | Hirai et al. | 560/24 |

FOREIGN PATENT DOCUMENTS 1485108 9/1977 United Kingdom ...................... 560/25

Primary Examiner—G. T. Breitenstein
Attorney, Agent, or Firm—Gene Harsh; Joseph C. Gil; Bruce E. Harang

[57] ABSTRACT

The instant invention relates to an improved process for the preparation of urethanes by the reaction of aromatic nitro compounds with alcohols and carbon monoxide in the presence of catalyst systems which contain selenium.

6 Claims, No Drawings

PROCESS FOR THE PREPARATION OF URETHANES

BACKGROUND OF THE INVENTION

Urethanes have been prepared by the reaction of an alcohol with an aromatic isocyanate. The isocyanate was obtained by the reaction of phosgene with the corresponding primary amine which was prepared by reduction of the corresponding nitro compound. This conventional process has various disadvantages, including the toxicity and corrosive nature of phosgene and the formation of hydrogen chloride as a by-product. Moreover, certain aromatic amines have harmful biological properties and some of them tend to be oxidized by air in storage.

There have therefore been attempts to avoid the use of the highly toxic phosgene and to prepare urethane directly from the corresponding nitro compounds, alcohols and carbon monoxide. The processes according to U.S. Pat. No. 3,993,685 and German Offenlegungsschrift No. 2,603,574 use catalyst systems based on metals of the platinum group. Since these processes inevitably entail considerable losses of these highly expensive catalysts, they have hitherto not become widely used on a commercial scale.

In the process according to German Offenlegungsschrift No. 2,343,826, it is proposed to use a combination of selenium or sulphur, or compounds of these elements, with very large quantities of a base as the catalytically active system. The bases used include, for example, triethylamine and pyridine. In order to be able to start the reaction satisfactorily in the presence of these amines, however, it appears to be necessary to use them in relatively large quantities compared with the nitro compound used as starting material. If dinitrotoluene is used as the nitro compound, the quantity of amine used is equal to, or greater than, that of dinitrotoluene. The use of such large quantities of amine entails numerous problems of an economical nature and particularly with regard to the recovery process. Moreover, this process leads to the formation of by-products such as amino compounds and ureas if measurable quantities of water are present, e.g. as hydrates or in the free form. The process according to German Offenlegungsschrift No. 2,343,826 is therefore also for the most part unsuitable for use on a commercial scale.

In the process according to German Offenlegungsschrift No. 2,614,101, the reduction in yield of the desired urethanes due to the above-mentioned formation of by-products can be avoided by using a catalyst system which is composed of elementary selenium or a selenium compound and a promoter consisting e.g. of a bicyclic amidine and a carboxylic acid. Although the process according to German Offenlegungsschrift No. 2,614,101 enables higher yields of urethanes to be obtained than in the process according to German Offenlegungsschrift No. 2,343,826, it also gives rise to troublesome quantities of by-products due, in particular, to hydrolysis and secondary reactions of the urethane formed.

The process according to German Offenlegungsschrift No. 2,623,694 is regarded as a further development of the process according to German Offenlegungsschrift No. 2,614,101 in that the formation of by-products of urethanes by the use of aromatic amino compounds or aromatic urea compounds corresponding to these by-products is suppressed. Although this measure provides an improvement to the process according to German Offenlegungsschrift No. 2,614,101, the process according to German Offenlegungsschrift No. 2,623,694 still has serious disadvantages. In particular, it requires the use of large quantities of organic amidine salts which may cause trouble in working up the end products. Furthermore, the process of German Offenlegungsschrift No. 2,623,694 has the disadvantage of requiring the use of very large quantities of selenium or selenium compounds.

It was therefore an object of the present invention to provide an improved process for the production of urethanes from aromatic nitro compounds, alcohols and carbon monoxide which would not have the disadvantages mentioned above of the known processes and which, in particular, would enable the quantity of selenium or selenium compound required to be substantially reduced and would also enable, as far as possible quantitative urethane formation to be achieved in spite of the reduction in the quantity of catalyst used.

DESCRIPTION OF THE INVENTION

This problem was solved by the process according to the present invention which is particularly characterized by the fact that bicyclic amidines are added as catalyst components in the absence of acids, particularly carboxylic acids or phenols. It must be regarded as surprising that the use of bicyclic amidines enables the quantity of selenium or selenium compound to be reduced without the simultaneous presence of a carboxylic acid or a phenol since it was to be expected according to German Offenlegungsschrift No. 2,623,694 that it would be essential to use a phenol or a carboxylic acid at the same time.

The present invention therefore relates to a process for the preparation of urethanes by the reaction of aromatic nitro compounds with aliphatic, cycloaliphatic or araliphatic alcohols and carbon monoxide in the presence of selenium and/or selenium compounds and of catalyst systems which contain aromatic amino compounds and/or aromatic urea compounds, characterized in that the catalyst systems used are free from carboxylic acids and phenols and contain bicyclic amidines as free bases.

The following can be used as starting compounds for the process according to the present invention.

1. Aromatic nitro compounds, e.g. nitrobenzene, 1,3-dinitrobenzene, o-nitrotoluene, m-nitrotoluene, p-nitrotoluene, 2,4-dinitrotoluene, 2,6-dinitrotoluene, nitronaphthalenes, nitroanthracenes, nitrobiphenylenes and the like. Nitro compounds suitable for the process according to the invention generally have a molecular weight of from 123 to 400 and contain from 1 to 3 aromatic nuclei, as well as from 1 to 3 nitro groups attached to aromatic nuclei and optionally also other substituents which are inert under the reaction conditions of the process of the invention. Among the preferred nitro compounds for the process according to the invention are nitrobenzene and the above-mentioned dinitrotoluenes. Any mixtures of the above-mentioned nitro compounds may, of course, also be used.

2. Aliphatic, cycloaliphatic or araliphatic alcohols, including any organic compound having a molecular weight within the range of from 32 to 311 which has at least one aliphatically, cycloaliphatically or araliphatically bound hydroxyl group and which is otherwise inert under the reaction conditions. Examples of suitable alcohols include primary, secondary and tertiary alcohols, e.g. methanol, ethanol, n-propanol, isopropanol, the various isomeric butanols, cyclohexyl alcohol, benzyl alcohol, hexyl alcohol, lauryl alcohol, or cetyl alcohol. Monohydric alcohols are preferably used in the process according to the invention, particularly ethanol.

3. Gaseous carbon monoxide.

The catalyst systems used in the process according to the present invention contain (a) selenium or a selenium compound, (b) a bicyclic amidine and (c) an aromatic amino compound and/or an aromatic urea compound.

Suitable catalyst components (a) include either elementary selenium in any form, preferably in the metallic form, or inorganic selenium compounds such as selenium dioxide or carbonyl selenide (COSe). Organic selenium compounds such as dimethylselenide or diphenylselenide could also be used, but elementary selenium and selenium dioxide are particularly preferred.

The catalyst components (b) are preferably bicyclic amidines corresponding to the following general formula:

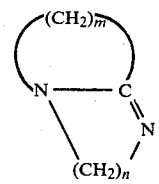

wherein:

m represents an integer of from 3 to 5; and n represents an integer from 2 to 4.

1,5-Diazabicyclo[4,3,0]-non-5-ene and 1,8-diazabicyclo[5,4,0]-undecene-7 are examples of such preferred bicyclic amidines.

The catalyst component (c) may be any organic compound which has aromatically bound primary amino groups and/or aromatically bound urea groups, and may in addition contain nitro groups and urethane groups. Component (c) of the catalyst systems to be used according to the present invention is generally a compound or mixture of compounds corresponding to the following general formulae:

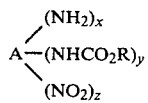

and/or

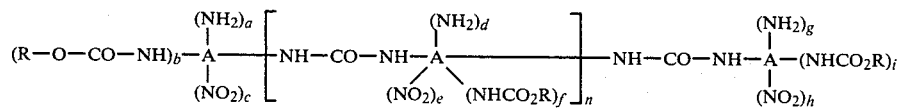

In these formulae:

x=1 or 2, y=0 or 1, z=0 or 1 and the sum of x+y+z is preferably 1 or 2;

a,b,c,d,e,f,g,h and i each represents 0 or 1 and the sum of a+b+c is equal to the sum of g+h+e and amounts to 0, 1 or 2, and if a+b+c=1 or 2, then the sum of d+e+f is less by 1, i.e. or 0 or 1, and it is 0 when a+b+c=0, and n=0, 1, 2, or 3 but preferably 0, A represents a monovalent, divalent or trivalent (preferably mono- or divalent) aromatic hydrocarbon group which may be substituted by $C_1$–$C_4$-alkyl and preferably corresponds to the aromatic hydrocarbon group of the aromatic nitro compound used in the process according to the present invention and R represents an aliphatic, cycloaliphatic or araliphatic hydrocarbon group generally having up to 18 carbon atoms and preferably corresponding to the hydrocarbon group of the alcohol component used in the process according to the present invention.

The following are examples of suitable catalyst components (c): aniline, o-, m- or p-toluidine, the isomeric nitroanilines, the isomeric diaminobenzenes, N,N'-diphenylurea, N,N'-bis-(2-methyl-5-nitro phenyl)-urea, N,N'-bis-(2-methyl-5-ethoxycarbonylamino-phenyl)-urea, N,N'-bis-(2-methyl-5-amino-phenyl)-urea, 2-amino-4-nitrotoluene, 4-amino-2-nitro-toluene, 2-amino-4-ethoxy-carbonylaminotoluene, 4-amino-2-ethoxycarbonylaminotoluene, 2,4-diaminotoluene, N,N'-bis-(3-nitro-4-methyl-phenyl)-urea, N,N'-bis-(2-methyl-5-nitrophenyl)-urea, N,N'-bis-(3-ethoxy-carbonylamino-4-methylphenyl)-urea, N,N'-bis-(2-methyl-5-ethoxycarbonylaminophenyl)-urea, N,N'-bis-(3-amino-4-methylphenyl)-urea, N,N'-bis-(2-methyl-5-aminophenyl)-urea, N-(3-nitro-4-methyl-phenyl)-N'-(2-methyl-5-nitro-phenyl)-urea, N-(3-ethoxycarbonylamino-4-methylphenyl)-N'-(2-methyl-5-ethoxycarbonylamino-phenyl)-urea, N-(3-amino-4-methylphenyl)-N'-(2-methyl-5-aminophenyl)-urea, N-(3-nitro-4-methyl-phenyl)-N'-(3-ethoxycarbonylamino-4-methyl-phenyl)-urea, N-(3-nitro-4-methylphenyl)-N'-(2-methyl-5-ethoxycarbonylamino-phenyl)-urea, N-(3-nitro-4-methyl-phenyl)-N'-(3-amino-4-methyl-phenyl)urea, N-(3-nitro-4-methyl-phenyl)-N'-(2-methyl-5-aminophenyl)-urea, N-(2-methyl-5-nitrophenyl)-N'-(3-ethoxycarbonyl-amino-4-methylphenyl)-urea, N-(2-methyl-5-nitrophenyl)-N'-(2-methyl-5-ethoxycarbonylamino-phenyl)-urea, N-(2-methyl-5-nitrophenyl)-N'-(3-amino-4-methyl-phenyl)-urea, N-(2-methyl-5-nitrophenyl)-N'-(2-methyl-5-aminophenyl)-urea, N-(3-ethoxycarbonylamino-4-methylphenyl)-N'-(2-methyl-5-aminophenyl)-urea, N-(2methyl-5-ethoxycarbonylamino-phenyl)-N'-(3-amino-4-methyl-phenyl)-urea, N-(2-methyl-5-ethoxycarbonylamino-phenyl)-N'-(2-methyl-5-amino-phenyl)-urea and any mixtures of the compounds exemplified above. As already mentioned, the preferred compounds (c) are those which correspond in their aromatic residue to the aromatic nitro compound used in the process according to the present invention. Thus, when using nitrobenzene, compound (c) may be aniline and/or diphenylurea, for example, whereas when compound (c) is used with nitrotoluene, it is a tolylamine and/or a ditolylurea. Similarly, when divalent nitro compounds such as 2,4-dinitrotoluene are used, the corresponding compounds containing disubstituted tolyl groups are preferably used as compound (c).

Higher homologues of the ureas mentioned as examples, i.e. compounds having several urea units, may also be used.

The reactants are generally used in such quantities in the process according to the present invention that from 1 to 50, preferably from 5 to 30 hydroxyl groups of the alcohol component are present for each nitro group of the aromatic nitro compound used as starting material. Carbon monoxide is generally used in excess.

Catalyst component (a), i.e. elementary selenium or the selenium compound, may be applied to a suitable carrier such as carbon, aluminum oxide, silicon dioxide, diatomaceous earth, activated clay, zeolite, molecular sieves, barium sulphate, calcium carbonate, iron exchange resins or similar materials. Component (a) is used in a quantity corresponding to from 0.1 to 50% by weight, preferably from 0.1 to 20% by weight of selenium, most preferably from 0.1 to 3% by weight of selenium, based on the quantity of nitro compound used as starting material.

The quantity of catalyst component (b), i.e. of bicyclic amidine used in the reaction mixture is generally from 1 to 40 mol %, preferably from 4 to 20 mol %, based on the nitro compound used as starting material.

Catalyst component (c) is generally present in the reaction mixture in a quantity of from 1 to 40%, preferably from 4 to 25 mol %, based on the nitro compound used as the starting material.

The process according to the present invention may be carried out without a solvent since alcohol itself serves as a solvent, although a separate solvent may be used if desired. Examples of such solvents include aromatic solvents such as benzene, toluene, or xylene, etc., nitriles such as acetonitrile, or benzonitrile, etc., sulphones such as Sulpholan, aliphatic halogenated hydrocarbons such as 1,1,2-trichloro-1,2,2-trifluoroethane, aromatic halogenated hydrocarbons such as monochlorobenzene, dichlorobenzene, or trichlorobenzene, etc., ketones, esters and other solvents such as tetrahydrofuran, 1,4-dioxane, 1,2-dimethoxyethane and the like.

There is no restriction on the sequence in which the starting materials and catalyst system are added and it may be varied according to the nature of the apparatus used. A starting mixture of, for example, alcohol, selenium catalyst, amine and/or urea compound, amidine and organic nitro compound may be introduced into a suitable pressure resistant reactor such as an autoclave, and carbon monoxide may then be introduced under pressure. The reaction mixture may then be stirred while it is heated until urethane formation is completed. The carbon monoxide may be introduced either semi-continuously or continuously into the reactor while the carbon dioxide formed in the reaction is removed. The reaction may be carried out either batchwise or semi-continuously or continuously. The carbon monoxide present in excess at the end of the reaction may be recycled.

The reaction temperature is generally maintained within a range of from 80° to 220° C., preferably from 120° to 200° C. Although the reaction proceeds more rapidly at higher reaction temperatures, there is a tendency to thermal decomposition at temperatures above 220° C., whereby the yield of urethane product is reduced. The reaction pressure, i.e. the initial carbon monoxide pressure, is generally in the range of from 10 to 300 bar, preferably from 20 to 150 bar. The reaction time depends upon the nature of the nitro compound used, the reaction temperature, the reaction pressure, the nature and quantity of the catalyst and the nature of the apparatus. It is however, generally within the range of from 5 minutes to 6 hours. After termination of the reaction which is indicated by a constant pressure (no further CO-consumption), the reaction mixture is either left to cool or actively cooled. When the gas which has been introduced into the reaction mixture has been discharged, the reaction mixture is separated by filtration, distillation or some other suitable method to separate the urethane formed from unreacted materials, by-products, solvents and catalyst.

The reaction mixture left behind after removal of the urethane contains the amino and urea compounds as well as any urethane which has not been removed. By returning these residues to be used again, the renewed addition of amino and/or urea compounds to the next batch of reaction system can be obviated. This method of recovering the residues is particularly advantageous for a continuous process.

When carrying out the process according to the present invention, care should be taken to exclude water. This is because if water is present, the possibility of partial hydrolysis of the products according to the invention cannot be eliminated in spite of the addition of catalyst component (c).

The essential feature of the invention in the process is to be seen in the use of "free" bicyclic amidine. In addition to its excellent catalytic activity, this promoter enables a very substantial reduction in the quantity of selenium to be activated in the catalyst system. The importance in the present invention of bicyclic amidine is demonstrated by the fact that other tertiary amines, e.g. diazabicyclo[2,2,2] octane or pyridine, cause a very substantial reduction in the activity of the catalyst system. Moreover, this essential role of the "free" amidine is completely unexpected. There is, at present, no plausible explanation available for this surprising effect of these compounds, particularly since "free" amidines have explicitly been described as ineffective.

The products of the process according to the present invention are valuable intermediate products for the preparation of pesticides or polyurethanes. They are particularly suitable as starting materials for the preparation of the corresponding isocyanates or polyisocyanates by the known method of splitting off of the alcohol component.

The following examples illustrate the invention without restricting it. All the reactions given in the examples were carried out in a stainless steel autoclave equipped with a stirrer. The yields given in the examples were calculated in each case on the results of gas chromatography and liquid chromatography. 1,5-Diazabicyclo-[4,3,0]-non-5-ene is referred to as DBN and 1,8-diazabicyclo[5,4,0]-undecene-7 as DBU.

EXAMPLES

EXAMPLE 1

17.50 g of a nitrobenzene, 2.10 g of DBU, 0.14 g of metallic selenium, 2.66 g of aniline and 140 g of dry ethanol were introduced into a 0.7 liter autoclave. The air in the autoclave was replaced by gaseous nitrogen and then by carbon monoxide. Following this, carbon monoxide was forced into the autoclave under pressure until the starting pressure was 70 bar at room temperature. The system was heated to 170° C. while it was being stirred, and was then stirred at 170° C. for a further 20 minutes.

A fall in pressure was observed during this time. The reaction solution was cooled to room temperature and the gas in the reaction system was replaced by nitrogen. The reaction solution was then discharged from the autoclave. After removal of the solid selenium by filtration, the filtrate was subjected to gas chromatographic analysis which showed that 100% of the nitrobenzene had been converted and the filtrate contained 23.96 g of ethyl-N-phenylcarbamate. Of the aniline introduced into the process, 2.01 g were left in the reaction solution.

Comparison Example 1A

Example 1 was repeated using an organic salt consisting of 2.10 g of DBU and 0.84 g of acetic acid. 52.7% of the nitrobenzene was converted. The filtrate contained 15.2 g of ethyl-N-phenylcarbamate and 0.43 g of aniline.

Comparison Example 1B

Example 1 was repeated without the addition of aniline. 26.1% of the nitrobenzene was converted. The filtrate contained 2.12 g of ethyl-N-phenylcarbamate.

Comparison Example 1C

Example 1 was repeated using 1.54 g of diazabicyclo [2,2,2]octane instead of DBU. 13.3% of the nitrobenzene was converted. The filtrate contained 4.0 g of ethyl-N-phenylcarbamate and 1.18 g of aniline.

Comparison Example 1D

Example 1 was repeated using 1.09 g of pyridine instead of DBU. Only 3.6% of the nitrobenzene was converted. The filtrate contained 0.56 g of ethyl-N-phenylcarbamate and 2.23 g of aniline.

EXAMPLE 2

Example 1 was repeated using 1.71 g of DBN instead of DBU. 98.9% of the nitrobenzene was converted. The filtrate contained 25.00 g of ethyl-N-phenylcarbamate and 0.77 g of aniline.

EXAMPLE 3

Example 1 was repeated using 1.05 g of DBU. The nitrobenzene was converted quantitatively and the filtrate was found to contain 23.7 g of ethyl-N-phenylcarbamate and 1.22 g of aniline.

EXAMPLE 4

Example 1 was repeated, but using 6 g of N,N'-diphenyl-urea instead of aniline. The reaction system was stirred at 170° C. for one hour and worked up as described in Example 1. The filtrate contained 29.5 g of ethyl-N-phenylcarbamate; the nitrobenzene was converted quantitatively.

EXAMPLE 5

17.5 g of nitrobenzene, 1.05 g of DBU, 0.7 g of metallic selenium, 2.66 g of aniline and 140 g of dry ethanol were stirred at 160° C. for 30 minutes as described in Example 1. Gas chromatographic analysis showed that a quantitative conversion of a nitrobenzene occurred. The filtrate contained 24.7 g of ethyl-N-phenylcarbamate and 0.31 g of aniline.

EXAMPLE 6

Example 5 was repeated using 1 g of selenium dioxide instead of metallic selenium. Nitrobenzene was converted quantitatively and the filtrate contained 23.6 g of ethyl-N-phenylcarbamate and 1.02 g of aniline.

EXAMPLE 7

25.46 g of 2,4-dinitrotoluene, 3.32 g of DBU, 0.7 g of metallic selenium, 3.5 g of 2,4-diaminotoluene and 140 g of dry ethanol were introduced into a 0.7 liter autoclave. The air in the autoclave was replaced by gaseous nitrogen and then by carbon monoxide. Thereafter, carbon monoxide was introduced into the autoclave under pressure until the starting pressure of 100 bar at room temperature was reached. The reaction system was heated and stirred at 170° C. for 2 hours. After removal of selenium by filtration liquid gas chromatography analysis showed a quantitative conversion of b 2,4-dinitrotoluene. The reaction solution contained 29.7 g of 2,4-diethoxycarbonylamine-toluene, 2.1 g of 2-nitro-4-ethoxycarbonyl amino-toluene and 0.1 g of 4-nitro-2-ethoxycarbonylamino-toluene.

What is claimed is:

1. In a process for the preparation of urethanes by the reaction of aromatic nitro compounds with aliphatic, cycloaliphatic or araliphatic alcohols and carbon monoxide in the presence of a catalyst system, the improvement wherein said reaction is conducted in the absence of carboxylic acids and phenols and said catalyst system comprises (1) selenium or a selenium compound; (2) a bicyclic amidine; and (3) an aromatic amino and/or aromatic urea compound.

2. The process of claim 1, characterized in that the aromatic nitro compound used is nitrobenzene.

3. The process of claim 1, characterized in that the aromatic nitro compound used is dinitrotoluene.

4. The process of claim 1, characterized in that the alcohol used is ethyl alcohol.

5. The process of claim 1 wherein component (1) is used in an amount of from 0.1 to 50% by weight based on the quantity of nitro compound, component (2) is used in a quantity of from 1 to 40 mol percent based on the amount of nitro compound, and component (3) is used in a quantity of from 1 to 40 mol percent based on the amount of nitro compound.

6. The process of claim 5 wherein the reaction temperature is from 80° to 220° C., the reaction pressure is from 10 to 300 bar and the reaction time is from 5 minutes to 6 hours.

* * * * *